United States Patent [19]

Baldwin et al.

[11] Patent Number: 4,593,039

[45] Date of Patent: Jun. 3, 1986

[54] 1-ARYLOXY-3-(SUBSTITUTED AMINOALKYLAMINO)-2-PROPANOLS

[75] Inventors: John J. Baldwin, Gwynedd Valley; Sandor L. Varga, Harleysville; Gerald S. Ponticello, Lansdale, all of Pa.

[73] Assignee: Merck & Co., Inc., Rahway, N.J.

[21] Appl. No.: 596,200

[22] Filed: Apr. 2, 1984

[51] Int. Cl.$^4$ .................. C07D 285/10; A61K 31/41
[52] U.S. Cl. ............................ 514/362; 548/135; 544/60; 544/134; 544/164; 544/182; 544/297; 544/367; 544/330; 546/209; 546/225; 546/230; 564/26; 564/225; 514/222; 514/242; 514/253; 514/255; 514/272; 514/326
[58] Field of Search ................... 548/135; 424/269

[56] References Cited

U.S. PATENT DOCUMENTS

| | | | |
|---|---|---|---|
| 3,337,628 | 8/1967 | Crowther et al. | 548/575 |
| 3,655,663 | 4/1972 | Wasson | 424/248.51 |
| 3,729,477 | 4/1973 | Wasson | 548/135 |
| 3,794,650 | 2/1974 | Meyer et al. | 546/174 |
| 3,828,095 | 8/1974 | Boschetti et al. | 424/319 |
| 3,832,470 | 8/1974 | Russek | 424/285 |
| 3,836,666 | 9/1974 | Koppe et al. | 424/282 |
| 3,850,945 | 11/1974 | Edwards | 548/185 |
| 3,850,946 | 11/1974 | Edwards | 548/186 |
| 3,850,947 | 11/1974 | Edwards | 548/186 |
| 3,852,291 | 12/1974 | Augstein et al. | 424/272 |
| 3,928,412 | 12/1975 | Smith | 424/321 |
| 3,941,789 | 3/1976 | Renth et al. | 544/370 |
| 4,083,992 | 4/1978 | Smith | 260/501.17 |
| 4,411,899 | 10/1983 | Baldwin et al. | 548/135 |
| 4,440,774 | 4/1984 | Baldwin | 544/370 |

FOREIGN PATENT DOCUMENTS

| | | | |
|---|---|---|---|
| 73971 | 3/1983 | European Pat. Off. | 548/135 |
| 8301772 | 5/1983 | European Pat. Off. | 548/135 |
| 2117769 | 10/1983 | European Pat. Off. | 548/135 |

OTHER PUBLICATIONS

Burger, A., Medicinal Chemistry, 2nd ed., p. 42, (1960) Interscience Publishers, Inc., N.Y.

*Primary Examiner*—George F. Lesmes
*Assistant Examiner*—S. A. Gibson
*Attorney, Agent, or Firm*—Alice O. Robertson; William H. Nicholson; Michael C. Sudol

[57] ABSTRACT

1-Aryloxy-3-(substituted aminoalkylamino)-2-propanols and pharmaceutically acceptable salts thereof have β-adrenergic blocking activity with some cardioselectivity and hence are useful as antihypertensive, antianginal, antiarrhythmic and cardioprotective agents and in the treatment of elevated intraocular pressure such as glaucoma.

17 Claims, No Drawings

1-ARYLOXY-3-(SUBSTITUTED AMINOALKYLAMINO)-2-PROPANOLS

SUMMARY OF THE INVENTION

This invention is concerned with novel compounds of structural formula:

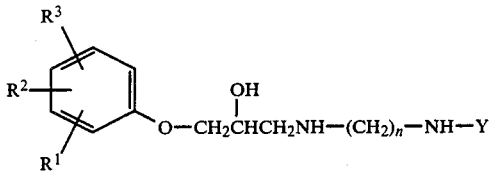

and pharmaceutically acceptable salts thereof, wherein $R^1$, $R^2$, $R^3$, n and Y are as defined below, which have β-adrenergic blocking activity with some cardioselectivity and hence useful as antihypertensive, antianginal, antiarrhythmic and cardioprotective agents, and in the treatment of elevated intraocular pressure such as glaucoma.

The invention is also concerned with processes for the preparation of the novel compounds; pharmaceutical formulations comprising one or more of the novel compounds as active ingredient; and a method of treating hypertension, arrhythmia, post myocardial infarction, angina and elevated intraocular pressure such as glaucoma by administration of a novel compound or pharmaceutical formulation thereof.

BACKGROUND OF THE INVENTION

A class of pharmaceutical agents known as β-adrenergic blocking agents, are available which affect cardiac, vascular and pulmonary functions and are mild antihypertensives. Specifically, these agents have the capability of reducing heart rate, without counteracting vasodepression or suppressing bronchodilation. β-adrenergic blocking agents, their chemical structure and activity, are disclosed in "*Clinical Pharmacology and Therapeutics*" 10, 292-306 (1969). Various β-adrenergic blocking agents are also described in the following U.S. Pat. Nos. 3,048,387; 3,337,628; 3,655,663; 3,794,650; 3,832,470; 3,836,666; 3,850,945; 3,850,946; 3,850,947; 3,852,291; 3,928,412; 4,134,983; 4,199,580; British Pat. No. 1,194,548; EP 42,592; and South African 74/1070.

Now, with the present invention there are provided novel β-blocking agents; processes for their synthesis, pharmaceutical formulations comprising one or more of the novel compounds; and methods of treatment with the novel compounds or pharmaceutical compositons thereof wherein an antihypertensive, antianginal, antiarrhythmic, cardioprotective, or antiglaucoma agent is indicated.

DETAILED DESCRIPTION OF THE INVENTION

The novel compounds of this invention are represented by the formula I:

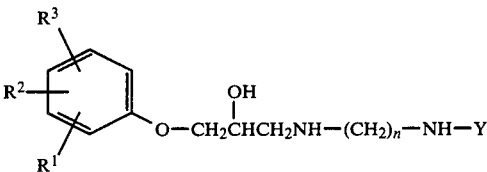

or a pharmaceutically acceptable salt thereof, wherein: Y is (1)

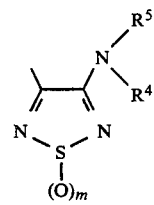

wherein m is 1 or 2,

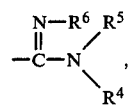  (2)

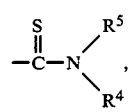  (3)

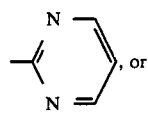  (4)

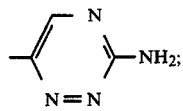  (5)

n is 1 to 8
$R^1$ is
(1) hydrogen,
(2) hydroxy, or
(3) hydroxymethyl;
$R^2$ and $R^3$ are independently:
(1) hydrogen,
(2) halo such as chloro, bromo or fluoro,
(3) hydroxy,
(4) amino,
(5) di($C_{1-5}$alkyl)amino,
(6) mono($C_{1-5}$alkyl)amino,
(7) nitro,
(8) cyano,
(9) $C_{1-6}$alkyl,
(10) $C_{3-8}$cycloalkyl,
(11) $C_{2-5}$alkenyl,
(12) $C_{1-4}$alkoxy,
(13) $C_{1-4}$alkylthio,
(14) $C_{2-5}$alkenyloxy,
(15) $C_{1-5}$alkanoyl, such as formyl, pentanoyl or the like;
$R^4$ and $R^5$ are independently:
(1) hydrogen,
(2) $C_{1-6}$alkyl, either unsubstituted or substituted with:

(a) hydroxy,
(b) $C_{1-4}$alkoxy, or
(c) phenyl;

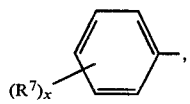 (3)

wherein X is 0, 1 or 2;

$R^4$ and $R^5$ are joined together to form a 5 or 6 membered ring with the nitrogen to which they are attached, the 6-membered ring optionally including another heteroatom selected from O, S and $C_{1-3}$alkyl-N, such as morpholino, N-methylpiperazino, pyrrolidino, or piperidino;

$R^6$ is
(1) —CN,
(2)

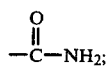

and $R^7$ is
(1) $C_{1-6}$alkyl,
(2) $C_{1-4}$alkoxy, or
(3) halo, such as chloro, bromo or fluoro, In a preferred embodiment of the compound of this invention $R^1$ is hydrogen; $R^2$ and $R^3$ are selected from hydrogen, halo, cyano, nitro and $C_{1-5}$alkanoyl; n is 2, and Y is:

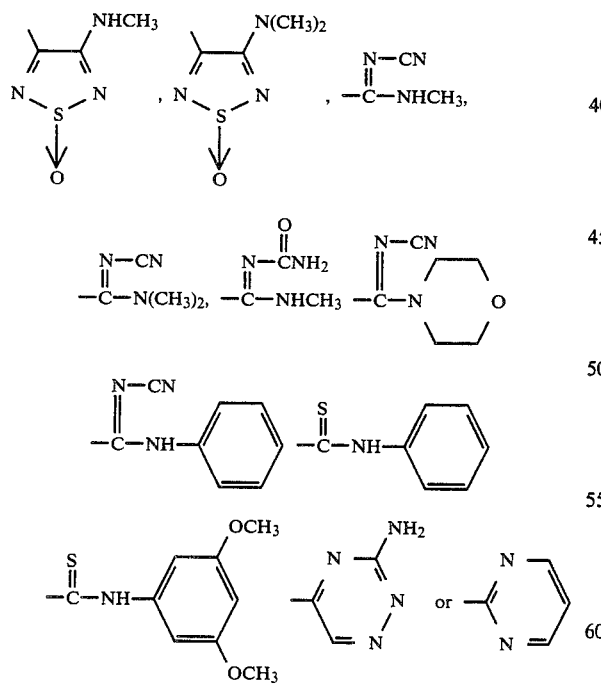

In an even more preferred embodiment, $R^1$ and $R^2$ are hydrogen, $R^3$ is cyano, n is 2 and Y is as defined in the preferred embodiment.

The novel compounds of this invention include all the optical isomer forms as pure enantiomers or as mixtures containing the optical isomers such as racemic mixtures and compounds.

The compounds of the present invention also include the non-toxic pharmaceutically acceptable acid addition and quaternary ammonium salts. The acid addition salts are prepared by treating the compounds with an appropriate amount of a suitable organic or inorganic acid. Examples of useful organic acids are carboxylic acids such as maleic acid, tartaric acid, acetic acid, pamoic acid, oxalic acid, propionic acid, salicyclic acid, succinic acid, citric acid, malic acid, isethionic acid, and the like. Useful inorganic acids are hydrohalo acids such as hydrochloric, hydrobromic, hydriodic, sulfuric, phosphoric acid, or the like.

Compounds of the present invention may be prepared by any convenient method, however, the preferred methods utilized will depend upon the $R^1$, $R^2$, $R^3$, $R^4$, $R^5$ and Y groups and n. In the methods described below, the $R^1$-$R^5$ and Y groups and n are as defined above unless otherwise indicated. Also, unless otherwise indicated, the starting materials employed are known in the literature, are commercially available, or can be prepared by methods known to those skilled in the art.

METHOD A:

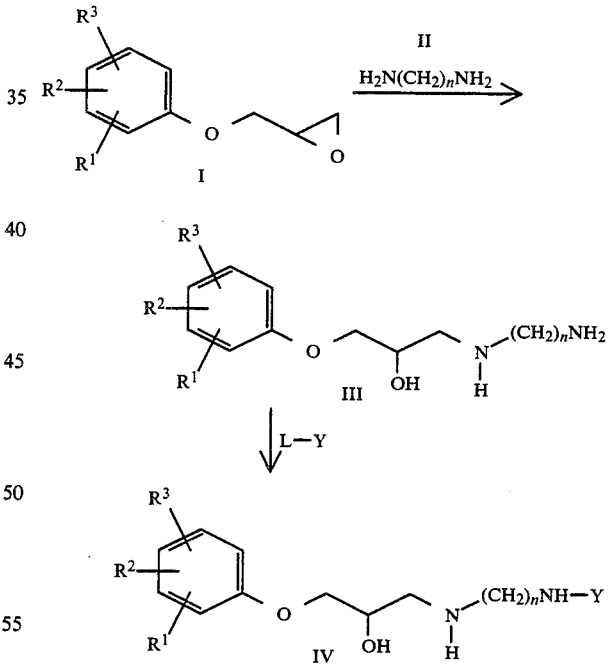

For Method A, an epoxide I is reacted with a diamine of the type II in a suitable solvent such as methanol, ethanol, isopropanol, methylene chloride, THF or the like, at 0° C. to the reflux temperature of the solvent for about 1–48 hours, preferably in isopropanol at 45° C. for 18 hours, to yield III. Compound III can then be reacted with L-Y wherein L is a leaving group such as ethoxy, chloro, bromo, methylthio, or the like, and Y is as defined below, to yield IV. Examples of Y are:

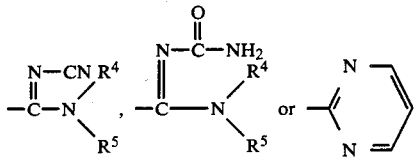

METHOD B:

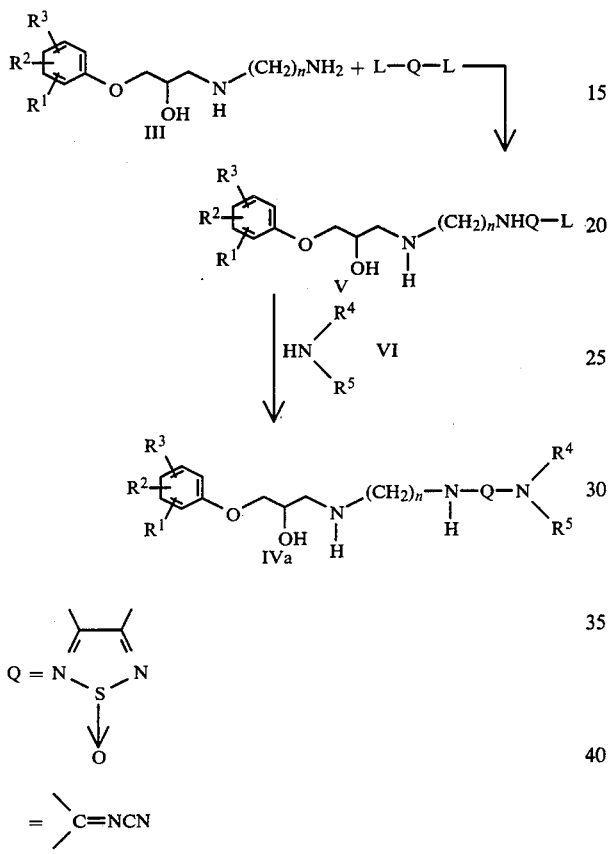

In Method B, the order in which the leaving groups are displaced is reversed. For example, amine III is reacted first with L-Q-L as defined above, and then in a last step with amine VI to yield IVa. The conditions utilized are the same as described in Method A.

METHOD C:

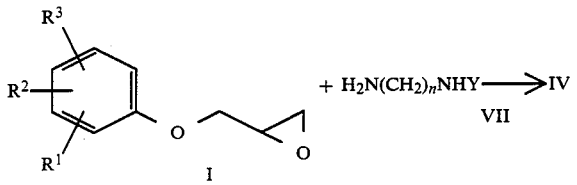

For Method C, epoxide I is reacted with a diamine of the type VII to yield IV by the conditions described in Method A.

The β-adrenergic blocking properties of the novel compounds of this invention indicates that they are useful in the treatment of conditions such as hypertension, angina pectoris or certain arrhythmias which are known to be amenable to treatment with β-adrenergic blocking agents.

For use as β-adrenergic blocking agents, the present compounds can be administered orally, transdermally, or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; as liquids dissolved or dispersed or emulsified in a suitable liquid carrier; in capsules encapsulated in a suitable encapsulating material; or (b) for parenteral administration dissolved or dispersed in a suitable liquid carrier such as solution or as an emulsion, or (c) as an aerosol or patch for transdermal administration. The ratio of active compound to compounding ingredients; i.e., carrier, diluent, etc., will vary as the dosage form requires. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

EXAMPLE 1

3-Methylamino-4[[2-[3-(2-cyanophenoxy)-2-hydroxy-propylamino]ethyl]amino]-1,2,5-thiadiazole-1-oxide hemihydrate, (4)

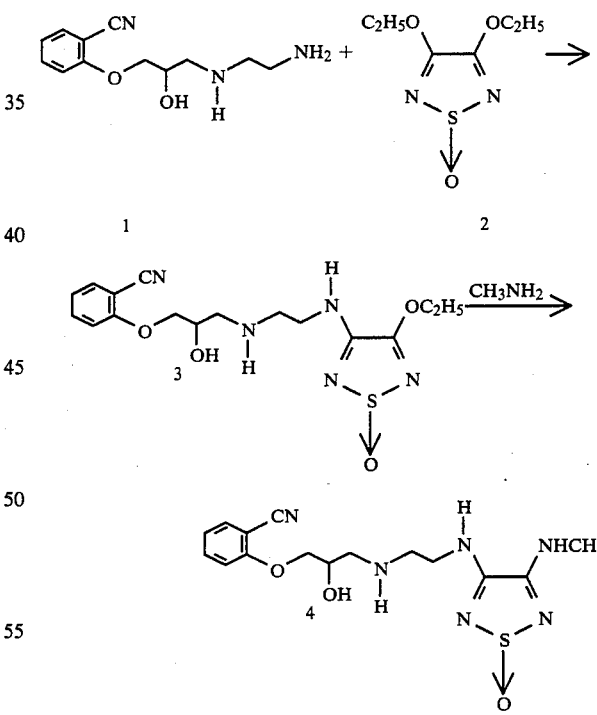

To 1 (1.76 g, 7.5 mmole) in 2-propanol (10 ml) the diethoxythiadiazole oxide, 2, in 2-propanol (20 ml) was added. The mixture was stirred at room temperature for 1 hour then $CH_3NH_2$ was bubbled through the solution for 1 hour. The solvent was removed in vacuo and the residue was purified on silica gel 60 by eluting with $CHCl_3$-$CH_3OH$-$H_2O$ (70-30-3 v:v:v) to yield 1.82 g (63.9%) of product 4. Analysis satisfactory for $C_{15}H_{20}N_6O_3S.1/2H_2O$

EXAMPLE 2

3-Amino-4-[[2-[3-(2-cyanophenoxy)-2-hydroxypropylamino]ethyl]amino]-1,2,5-thiadiazole-1-oxide (0.25 CHCl$_3$)

Following the same procedure as in Example 1, the title compound was obtained by using ammonia instead of methylamine (64% yield). Analysis satisfactory for C$_{14}$H$_{18}$N$_6$O$_3$S.1/4CHCl$_3$.

EXAMPLE 3

N-Cyano-N'-[2-[3-(2-cyanophenoxy)-2-hydroxypropylamino]ethyl]-N''-methylguanidine, (8)

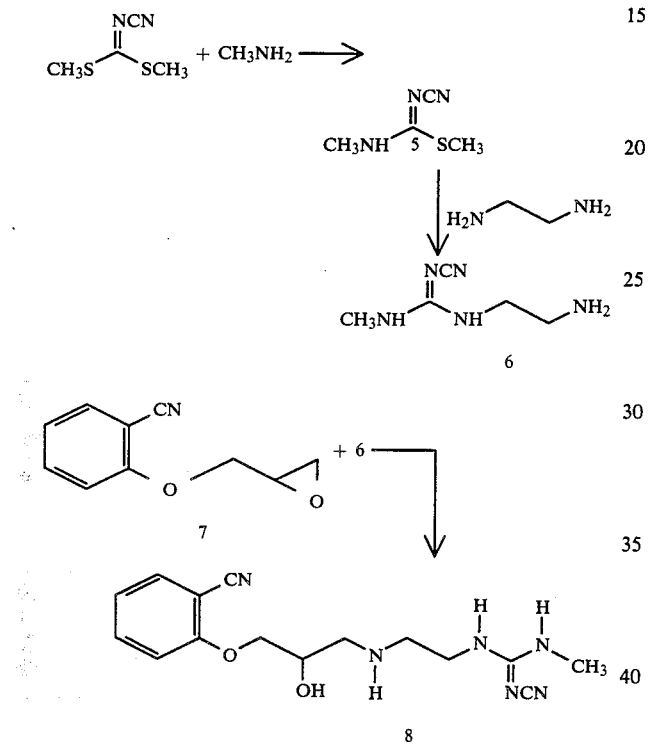

Step A: Preparation of N-(2-Aminoethyl)-N'-cyano-N''-methylguanidine

Methylamine (1.58 g, 50.9 mmole) was condensed into 20 ml of 2-propanol. To this solution, (CH$_3$S)$_2$C=NCN (7.44 g, 50.9 mmole) in 2-propanol (40 ml) was added (slight exotherm). The mixture was stirred for 15 minutes and then added dropwise over 15 minutes to 68.2 ml (1.02M) of ethylenediamine while stirring vigorously.

After 3½ hours the solvent and the excess ethylenediamine were removed in vacuo. The residue was evaporated to dryness in vacuo twice with 100 ml of 2-propanol then washed with ether (4×50 ml) and dried in vacuo to yield 7.0 g (97.4%) of 9.

Employing the procedure substantially as described in Example 3, Step A, but substituting dimethylamine for monomethylamine used therein, there is produced N-(2-aminoethyl)-N'-cyano-N''-dimethylguanidine.

Step B: Preparation of N-Cyano-N'-[2-[3-(2-cyanophenoxy)-2-hydroxypropylamino]ethyl]-N''-methylguanidine, (8)

The amine 6 (2.12 g, 15 mmole) in 2-propanol (30 ml) was heated to 40° C. and then the epoxide 7 (2.63 g, 15 mmole) in a mixture of 2-propanol (20 ml) and toluene (10 ml) was added dropwise to this solution. The reaction mixture was stirred at 40° C. for 6 hours. The solvent was removed in vacuo and the product was purified on a silica gel column using CHCl$_3$-CH$_3$OH-H$_2$O (70-30-3 v:v:v) as the eluent to yield 2.75 g (58%) of product 8; m.p. 128°–130° C. Analysis satisfactory for C$_{15}$H$_{20}$N$_6$O$_2$.¼H$_2$O.

EXAMPLE 4

N-Cyano-N'-[2-[3-(2-cyanophenoxy)-2-hydroxypropylamino]ethyl-N'',N''-dimethylguanidine Following the same procedure as in Example 3, Step B, the title compound was obtained in 4.5% yield by using N-(2-aminoethyl)-N'-cyano-N''-dimethylguanidine in place of N-(2-aminoethyl)-N'-cyano-N''-methylguanidine.

EXAMPLE 5

[[2-[[3-(2-Cyanophenoxy)-2-hydroxypropyl]amino]ethyl]-amino](methylamino)methylene urea, (10)

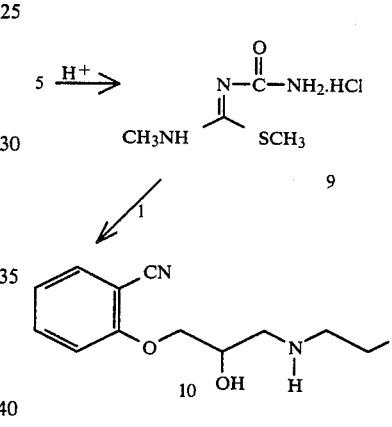

Step A: Preparation of N'-carbamoyl-S,N''-dimethylisothiourea, (9)

(CH$_3$NH) (CH$_3$S)C=NCN, 5, (3.23 g, 25 mmole) was dissolved in a mixture of H$_2$O (50 ml) and concentrated HCl (100 ml) and stirred overnight at room temperature. Another 50 ml concentrated HCl was added to the suspension and the mixture was stirred at room temperature for an additional 2 days. The aqueous solution was extracted with CHCl$_3$ (2×100 ml) and evaporated to dryness in vacuo to yield 4.4 g (95.6%) of 9.

Step B: Preparation of [[2-[[3-(2-cyanophenoxy-2-hydroxypropyl]amino]ethyl-]amino](methylamino)-methylene urea dihydrochloride, (10)

Compounds 1 (2.35 g, 10 mmole) and 9 (1.83 g, 10 mmole) were dissolved in 2-propanol (25 ml) and stirred overnight at room temperature. The solvent was removed in vacuo and the product purified on a silica gel 60 column using CH$_2$Cl$_2$-CH$_3$OH-H$_2$O (80-20-2 v:v:v) as the eluent to yield 0.9 g (24.3%) of product 10; m.p. 170° C. (dec.). Analysis satisfactory for C$_{15}$H$_{22}$N$_6$O$_3$.2HCl.1½H$_2$O.

EXAMPLE 6

N-[Cyanoimino-[[2-[[3-(2-cyanophenoxy)-2-hydroxypropyl]amino]ethyl]amino]]methylmorpholine, (11)

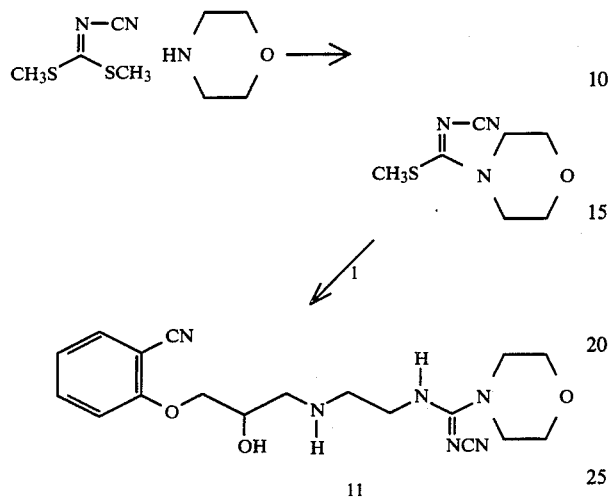

(CH₃S)₂C=NCN (2.19 g, 15 mmole) and morpholine (1.30 g, 15 mmole) were dissolved in 2-propanol (15 ml) and stirred at room temperature for 1 hour. The reaction mixture was diluted with 2-propanol (15 ml), heated to 45° C. and then 1 (3.53 g, 15 mmole) in 2-propanol (15 ml) was added. The reaction mixture was stirred overnight at 45° C., the solvent was removed in vacuo and the product purified on silica gel 60 using CH₂Cl₂-CH₃OH-H₂O (80-20-2 v:v:v) as the eluent. Crystallization from CH₃CN yielded 3.05 g of impure product which was rechromatographed on silica gel 60 using CHCl₃-CH₃OH-H₂O (90-10-1 v:v:v) as the eluent. Crystallization from CH₃CN-ether yielded 1.6 g (28.7%) of product 11. Analysis satisfactory for $C_{18}H_{24}N_6O_3$.

EXAMPLE 7

N-Cyano-N'-[2-[3-(2-cyanophenoxy)-2-hydroxypropylamino]ethyl]-N"-phenylguanidine Following the same procedure as in Example 6, the title compound was obtained by using aniline in place of morpholine. The title compound was purified by chromatography on silica gel 60 by elution with CHCl₃-CH₃OH-H₂O (80-20-2 v:v:v); m.p. 146°-147° C. Analysis satisfactory for $C_{20}H_{22}N_6O_2$.

EXAMPLE 8

N-2-[(3-(2-Cyanophenoxy)-2-hydroxypropyl)amino]-ethyl-N'-phenylthiourea

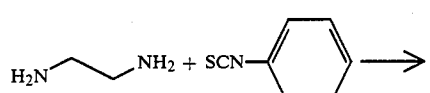

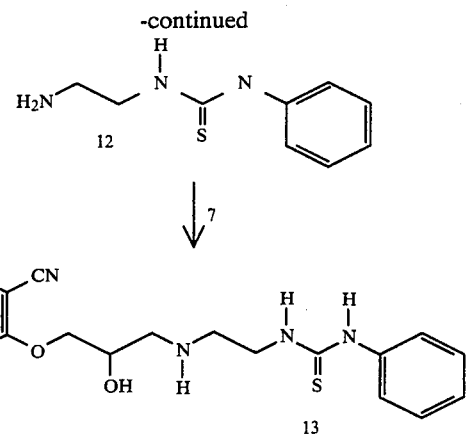

Step A: Preparation of N-(2-Aminoethyl)-N'-phenylthiourea, (12)

Compound 12 was prepared in 24% yield according to the procedure of O. Stoutland et al. [J. Org. Chem., (1959), 24 818] m.p., 131°-132°: (lit., 136°-137° C.).

Step B: Preparation of N-2-[(3-(2-cyanophenoxy)-2-hydroxypropyl)amino]ethyl-N'-phenylthiourea hydrate, (13)

A solution was prepared of 1.75 g (0.01 mole) of 2,3-epoxy-1-(2-cyanophenoxy)propane, 7, in 50 ml of isopropyl alcohol, assisted by gentle warming and sonication. To this was next added 2.95 g (0.01 mole) of 12 all at once. The solution was refluxed for one hour then stirred overnight at room temperature. The solution was concentrated in vacuo to 5.6 of gum, which was chromatographed over 150 g of silica gel using 10% CH₃OH/CHCl₃ (saturated with NH₃) and taking 10 ml fractions. Fractions 12-41 gave 1.8 g of a foam which was found to be nonhomogeneous. This material was rechromatographed over 200 g of silica gel using the same solvent system as before and taking 10 ml cuts. Fractions 12-30 gave 400 mg (12%) of yellow sticky 13, m.p. 41°-47° C. $R_f$=0.64 (silica gel GF, 10% CH₃OH/CHCl₃(NH₃)). Mass spectrum, m/e 370 (M+); liquid chromatography showed 98% pure. Analysis satisfactory for $C_{19}H_{22}N_4O_2S \cdot 1.6H_2O$.

EXAMPLE 9

N-2-[(3-(2-Cyanophenoxy)-2-hydroxypropyl)amino]ethyl-N'-(3,5-dimethoxyphenyl)thiourea 0.6 hydrate, (15)

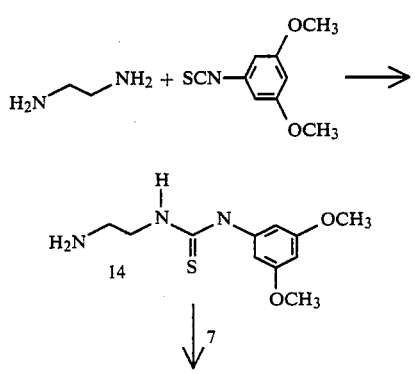

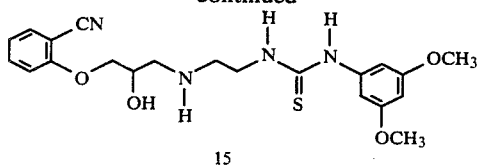

15

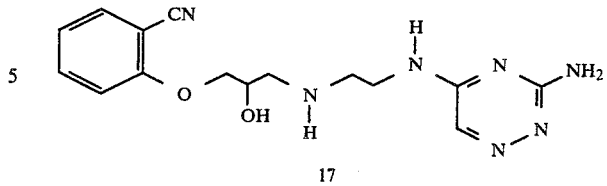

17

Step A: Preparation of N-(2-Aminoethyl)-N'(3,5-dimethoxyphenyl)thiourea, (14)

A slurry of 9.75 g (0.05 mole) of 3,5-dimethoxyphenyl isothiocyanate in 27 ml of ether was added dropwise to a stirred solution of 3.0 g (0.05 mole) of ethylenediamine at room temperature. A five-degree rise in temperature was noted at the start of the one hour addition period. A solid appeared during the addition, and stirring was continued for 2.5 hours. The batch was allowed to stand overnight, and 100 ml of H$_2$O was added. The solid was removed by filtration and the filtrate acidified with 4.5 ml of concentrated HCl and evaporated to dryness on the steam bath. The residue was sonicated with 100 ml of water and warmed to 50° C. for 10 minutes. This was filtered and basified to pH 10 with 10% NaOH. This gave 2.6 g of 14, m.p. 125°–126° C. Analysis satisfactory for C$_{11}$H$_{17}$N$_3$O$_2$S.

Step B: Preparation of N-2-[(3-(2-cyanophenoxy)-2-hydroxypropyl)amino]ethyl-N'-(3,5-dimethoxyphenyl)thiourea, (15)

A solution of 1.28 g (7.3 mmoles) of 2,3-epoxy-1-(2-cyanophenoxy)propane, 7, in 30 ml of isopropyl alcohol (warmed and sonicated) was treated with 1.86 g (7.3 mmoles) of 14 all at once. This was heated under reflux for 2 hours and stirred overnight at room temperature. After this, a small amount of solid (860 mg) was removed and the solution was concentrated to 2.3 g of semi-solid gum. This was chromatographed over 150 g of silica gel 60 using 10% (v/v) CH$_3$OH/CHCl$_3$ saturated with NH$_3$. Three fractions of 150 ml each were taken after an 800-ml forerun. The third fraction provided 1.31 g of a white foam. This was chromatographed again, taking 10-ml fractions. Cuts 17, 18 and 19 provided 80 mg (2.5%) of 15, m.p., 45°–55° C. Mass spectrum, m/e 430 (M+), base peak, m/e 195. Liquid chromatography showed 93.6% purity.

Analysis satisfactory for C$_{21}$H$_{26}$N$_4$O$_4$S.0.6H$_2$O.

EXAMPLE 10

3-Amino-5-(2-{3-[(2-cyanophenoxy)-2-hydroxypropyl]-amino}ethylamino)-1,2,4-triazine

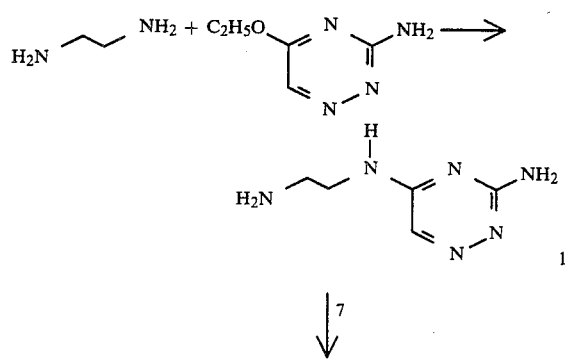

Step A: Preparation of 3-Amino-5-(2-amino-1-ethylamino)-1,2,4-triazine, (16)

To a slurry of 3-amino-5-ethoxy-1,2,4-triazine (1.40 g, 0.0100 mol) in xylene (5 ml) was added ethylenediamine (1.00 ml, 0.0150 mol). The mixture was stirred at 120° C. for 3.5 hours, cooled, and concentrated to dryness in vacuo. The residue was stirred under ether, filtered off, and dried to give the title product, 16, (1.47 g, 95%, m.p. 186°–191° C.). TLC (20% methanol/chloroform/ammonia, silica): R$_f$=0.14.

Step B: Preparation of 3-Amino-5-(2-{3-[(2-cyanophenoxy)-2-hydroxypropyl]amino}ethylamino)-1,2,4-triazine, (17)

To a solution of 3-(2-cyanophenoxy)propylene oxide (1.40 g, 0.0080 mol) in isopropanol (40 ml) was added a suspension of 3-amino-5-(2-amino-1-ethylamino)-1,2,4-triazine (1.23 g, 0.0080 mol) in isopropanol (30 ml). The resulting solution was heated at 40° C. for 18 hours. The warm mixture was then filtered and the insoluble material was washed with isopropanol (20 ml). The combined filtrate was concentrated in vacuo to leave 2.40 g of solid which was chromatographed on a column of silica gel 60 and eluted gradiently with 0–20% (v/v) methanol/chloroform followed by 20–50% methanol/chloroform saturated with ammonia. From the fraction eluted with 20% methanol/chloroform saturated with ammonia there was obtained the crude product 17 (0.47 g, 18%). The crude product was recrystallized from chloroform/ether to give the purified product, 17, (0.22 g, 8%, m.p. 115°–120° C.).

Analysis satisfactory for C$_{15}$H$_{19}$N$_7$O$_2$: TLC (20% methanol/chloroform, silica): R$_f$=0.23.

EXAMPLE 11

2-[2-[[3-(2-Cyanophenoxy)-2-hydroxypropyl]amino]ethylaminopyrimidine, (18)

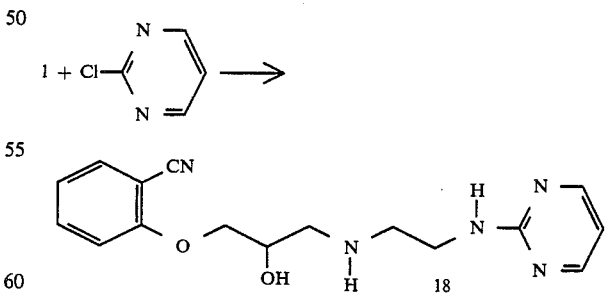

The amine 1 (1.52 g, 6.46 mmole) and 2-chloropyrimidine (740 mg, 6.46 mmole) were heated at 60° C. in 2-propanol (5 ml) for 4½ hours and then stirred at room temperature overnight. The mixture was heated at 60° C. for an additional 8½ hours. The solvent was removed in vacuo and the product was purified by chromatography on silica gel 60 using CH$_2$Cl$_2$-CH$_3$OH-H$_2$O (70-30-3 v:v:v) as the eluent to yield 870 mg (43%) of 18, m.p. 126°–128° C. Analysis satisfactory for $C_{16}H_{19}N_5O_2 \cdot 1.5H_2O$.

Following the procedures of the foregoing examples employing appropriate starting materials, there are produced the following compounds.

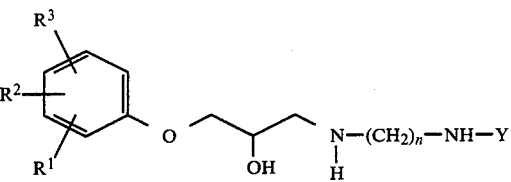

| R$^1$ | R$^2$ | R$^3$ | n | Y |
|---|---|---|---|---|
| H | H | F | 1 | $-\underset{\underset{\text{\scriptsize }}{\|}}{\overset{NCN}{C}}-N\bigcirc + HCH_3$ |
| HO | H | H | 2 | $-\underset{\underset{\text{\scriptsize }}{\|}}{\overset{NCN}{C}}-N(CH_3)_2$ |
| HOCH$_2$ | H | H | 3 | $-\underset{\underset{\text{\scriptsize }}{\|}}{\overset{NCONH_2}{C}}-NHCH_3$ |
| H | HO | H | 4 | $-\underset{\underset{\text{\scriptsize }}{\|}}{\overset{NCN}{C}}-NH-\text{Ph}$ |
| H | H | H$_2$N | 5 | $-\underset{\underset{\text{\scriptsize }}{\|}}{\overset{S}{C}}-NH-\text{Ph}$ |
| H | (CH$_3$)$_2$N | H | 6 | $-\underset{\underset{\text{\scriptsize }}{\|}}{\overset{S}{C}}-NH-\text{(3,5-(OCH}_3\text{)}_2\text{Ph)}$ |
| H | CH$_3$ | CH$_3$NH | 7 | triazine-NH$_2$ |
| H | O$_2$N— | C$_2$H$_5$ | 8 | pyrimidine |
| H | CH$_3$O | CH$_3$ | 1 | $-\underset{\underset{\text{\scriptsize }}{\|}}{\overset{NCN}{C}}-NHCH_3$ |
| H | H | C$_2$H$_5$ | 2 | $-\underset{\underset{\text{\scriptsize }}{\|}}{\overset{N}{C}}-N(CH_3)_2$ |
| H | n-C$_3$H$_7$ | H | 2 | $-\underset{\underset{\text{\scriptsize }}{\|}}{\overset{NCONH_2}{C}}-NHCH_3$ |
| H | H | n-C$_6$H$_{13}$ | 2 | $-\underset{\underset{\text{\scriptsize }}{\|}}{\overset{NCN}{C}}-NH-\text{Ph}$ |

-continued

| | | | | |
|---|---|---|---|---|
| R¹ | R² | R³ | n | Y |
| H | c-C₃H₅ | CH₃ | 2 | −C(=S)−NH−phenyl |
| H | H | c-C₆H₁₁ | 2 | −C(=S)−NH−(3,5-dimethoxyphenyl) |
| H | CH₃−CH=CH− | H | 2 | 3-amino-1,2,4-triazine |
| H | H | CH₃O | 2 | pyrimidin-2-yl |
| H | (CH₃)₂CH−O | H | 1 | −C(=NCN)−N(CH₃)₂ |
| H | H | C₂H₅S− | 2 | −C(=NCN)−N(CH₃)₂ |
| H | CH₃CH=CH−O− | H | 3 | −C(=NCONH₂)−NHCH₃ |
| H | H | CH₃C(=O) | 4 | −C(=NCN)−NH−phenyl |
| H | C₂H₅C(=O) | H | 5 | −C(=S)−NH−phenyl |

| INGREDIENT | AMOUNT (Mg.) |
|---|---|
| TABLET FORMULATION I | |
| 3-Methylamino-4[[2-[3-(2-cyano-phenoxy)-2-hydroxypropylamino]-ethyl]amino]-1,2,5-thiadiazole-1-oxide | 40.0 |
| calcium phosphate | 120.0 |
| CAPSULE FORMULATION | |
| [[2-[[3-(2-Cyanophenoxy)-2-hydroxy-propyl]amino]ethyl]amino](methyl-amino)methylene urea | 250 |
| lactose, U.S.P. | 93 |
| talc | 7 |
| INJECTABLE SOLUTION | |

-continued

| INGREDIENT | AMOUNT (Mg.) |
|---|---|
| N—[Cyanoimino-[[2-[3-(2-cyano-phenoxy)-2-hydroxypropyl]amino]-ethyl]amino]]methylmorpholine | 5 |
| sodium chloride | 9 |
| distilled water, q.s. | 1.0 ml. |
| LIQUID SUSPENSION | |
| N—2-[(3-(2-Cyanophenoxy)-2-hydroxy-propyl)amino]ethyl -N'—phenylthio-urea 1.6 hydrate | 5.0 |
| Veegum H.V. | 3.0 |
| methyl paraben | 1.0 |
| kaolin | 10.0 |
| glycerin | 250.0 |

| INGREDIENT | AMOUNT (Mg.) |
| --- | --- |
| water, q.s. | 1 liter |

What is claimed is:
1. A compound having the structural formula:

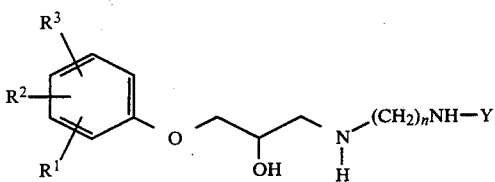

or a pharmaceutically acceptable salt thereof, wherein:
Y is (1)

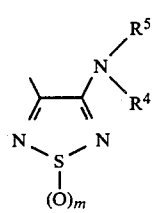

wherein m is 1 or 2,
n is 1–8;
$R^1$ is
  (1) hydrogen,
  (2) hydroxy, or
  (3) hydroxymethyl;
$R^2$ and $R^3$ are independently:
  (1) hydrogen,
  (2) halo,
  (3) hydroxy,
  (4) amino,
  (5) di($C_{1-5}$alkyl)amino,
  (6) mono($C_{1-5}$alkyl)amino,
  (7) nitro,
  (8) cyano,
  (9) $C_{1-6}$alkyl,
  (10) $C_{3-8}$cycloalkyl,
  (11) $C_{2-5}$alkenyl,
  (12) $C_{1-4}$alkoxy,
  (13) $C_{1-4}$alkylthio,
  (14) $C_{2-5}$alkenyloxy,
  (15) $C_{1-5}$alkanoyl;
$R^4$ and $R^5$ are independently:
  (1) hydrogen,
  (2) $C_{1-6}$alkyl, either unsubstituted or substituted with:
    (a) hydroxy,
    (b) $C_{1-4}$alkoxy, or
(3)

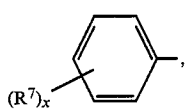

wherein X is 0, 1 or 2;
$R^4$ and $R^5$ are joined together to form a 5 membered ring with the nitrogen to which they are attached, $R^7$ is
  (1) $C_{1-6}$alkyl,
  (2) $C_{1-4}$alkoxy,
  (3) or halo.

2. The compound of claim 1 or a is pharmaceutically acceptable salt thereof wherein $R^1$ is hydrogen; $R^2$ and $R^3$ are halo, nitro, $C_{1-5}$alkanoyl, hydrogen or cyano; n is 2, and Y is:

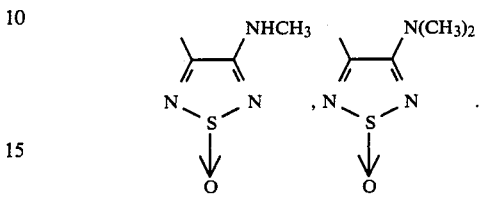

3. The compound of claim 2, or a pharmaceutically acceptable salt thereof wherein $R^1$ and $R^2$ are hydrogen; and $R^3$ is cyano.

4. A pharmaceutical β-blocking composition comprising a pharmaceutically acceptable carrier and an effective β-blocking amount of a compound of formula:

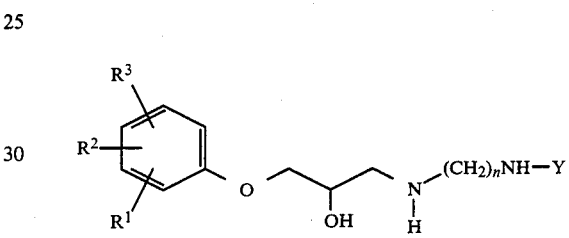

or a pharmaceutically acceptable salt thereof, wherein:
Y is (1)

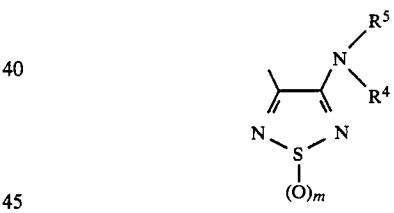

wherein m is 1 or 2,
n is 1–8;
$R^1$ is
  (1) hydrogen,
  (2) hydroxy, or
  (3) hydroxymethyl;
$R^2$ and $R^3$ are independently:
  (1) hydrogen,
  (2) halo,
  (3) hydroxy,
  (4) amino,
  (5) di($C_{1-5}$alkyl)amino,
  (6) mono($C_{1-5}$alkyl)amino,
  (7) nitro,
  (8) cyano,
  (9) $C_{1-6}$alkyl,
  (10) $C_{3-8}$cycloalkyl,
  (11) $C_{2-5}$alkenyl,
  (12) $C_{1-4}$alkoxy,
  (13) $C_{1-4}$alkylthio,
  (14) $C_{2-5}$alkenyloxy,
  (15) $C_{1-5}$alkanoyl;

$R^4$ and $R^5$ are independently:
(1) hydrogen,
(2) $C_{1-6}$alkyl, either unsubstituted or substituted with:
 (a) hydroxy,
 (b) $C_{1-4}$alkoxy, or
 (c) phenyl;
(3)

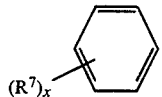

wherein X is 0, 1 or 2;
$R^4$ and $R^5$ are joined together to form a 5 membered ring with the nitrogen to which they are attached,
$R^7$ is
(1) $C_{1-6}$alkyl,
(2) $C_{1-4}$alkoxy, or
(3) halo.

5. The composition of claim 4 wherein $R^1$ is hydrogen, $R^2$ and $R^3$ are halo, nitro, $C_{1-5}$alkanoyl, hydrogen or cyano, n is 2, and Y is:

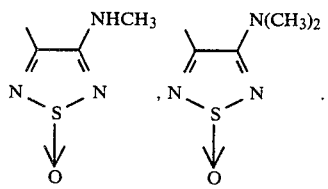

6. The composition of claim 5, wherein $R^1$ and $R^2$ are hydrogen, and $R^3$ is cyano.

7. A method of treating hypertension, angina, arrhythmia, post myocardial infarction and/or elevated intraocular pressure in a patient in need of such treatment which comprises administration of an antihypertensive amount of a compound of structural formula:

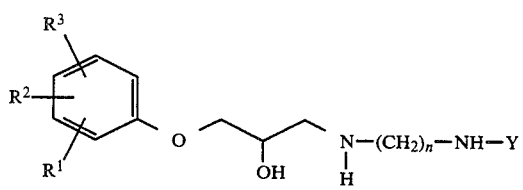

or a pharmaceutically acceptable salt thereof, wherein:
Y is (1)

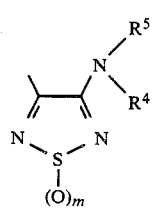

wherein m is 1 or 2,
n is 1-8
$R^1$ is
(1) hydrogen,
(2) hydroxy, or
(3) hydroxymethyl;

$R^2$ and $R^3$ are independently:
(1) hydrogen,
(2) halo,
(3) hydroxy,
(4) amino,
(5) di($C_{1-5}$alkyl)amino,
(6) mono($C_{1-5}$alkyl)amino,
(7) nitro,
(8) cyano;
(9) $C_{1-6}$alkyl,
(10) $C_{3-8}$cycloalkyl,
(11) $C_{2-5}$alkenyl,
(12) $C_{1-4}$alkoxy,
(13) $C_{1-4}$alkylthio,
(14) $C_{2-5}$alkenyloxy,
(15) $C_{1-5}$alkanoyl;
$R^4$ and $R^5$ are independently:
(1) hydrogen,
(2) $C_{1-6}$alkyl, either unsubstituted or substituted with:
 (a) hydroxy,
 (b) $C_{1-4}$alkoxy, or
 (c) phenyl;
(3)

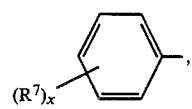

wherein X is 0, 1 or 2
$R^4$ and $R^5$ are joined together to form a 5 membered ring with the nitrogen to which they are attached,
$R^6$ is
(1) —CN,
(2)

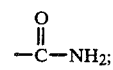

and
$R^7$ is
(1) $C_{1-6}$alkyl,
(2) $C_{1-4}$alkoxy or
(3) halo.

8. The method of claim 7 wherein $R^1$ is hydrogen $R^2$ and $R^3$ are hydrogen, halo, nitro, $C_{1-5}$-alkanoyl, or cyano; n is 2, and Y is:

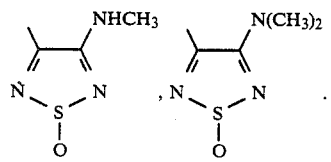

9. The method of claim 8 wherein $R^1$ and $R^2$ are hydrogen, and $R^3$ is cyano.

10. A compound according to claim 1 in which Y is

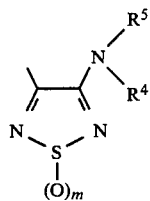

wherein m is 1 or 2.

11. A compound according to claim 10 in which $R^1$ is hydrogen; $R^2$ and $R^3$ are independently hydrogen, halo, nitro, $C_{1-5}$alkanoyl or cyano; n is 2; $R^4$ is hydrogen or methyl, $R^5$ is methyl, and m is 1.

12. A compound according to claim 11 in which $R^1$ and $R^2$ are hydrogen, and $R^3$ is cyano.

13. A composition according to claim 4 wherein Y is

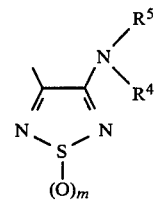

wherein m is 1 or 2.

14. A composition according to claim 13 wherein $R^1$ is hydrogen; $R^2$ and $R^3$ are independently halo, nitro, $C_{1-5}$alkanoyl, hydrogen or cyano; n is 2; $R^4$ is hydrogen or methyl, $R^5$ is methyl; and m is 1.

15. A composition according to claim 13 wherein $R^1$ and $R^2$ are hydrogen, and $R^3$ is cyano.

16. A method according to claim 7 wherein Y is

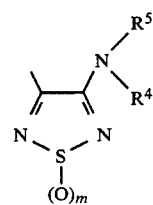

wherein m is 1 or 2.

17. A method according to claim 16 wherein $R^1$ is hydrogen; $R^2$ and $R^3$ are independently hydrogen, halo, nitro, $C_{1-5}$alkanoyl or cyano; n is 2; $R^4$ is hydrogen or methyl; $R^5$ is methyl and m is 1.

* * * * *

UNITED STATES PATENT AND TRADEMARK OFFICE
CERTIFICATE OF CORRECTION

PATENT NO. : 4,593,039

DATED : June 3, 1986

INVENTOR(S) : John J. Baldwin, et al.

It is certified that error appears in the above—identified patent and that said Letters Patent is hereby corrected as shown below:

Column 3, lines 18 - 25, the formula should read -- $R^6$ is (1) $-CN$, (2) $\underset{\|}{\overset{O}{-C}}-NH_2$;

and --.

Signed and Sealed this

Twenty-third Day of December, 1986

*Attest:*

DONALD J. QUIGG

*Attesting Officer*  *Commissioner of Patents and Trademarks*